(12) United States Patent
Milpied et al.

(10) Patent No.: US 11,198,009 B2
(45) Date of Patent: *Dec. 14, 2021

(54) ACTIVE IMPLANTABLE MEDICAL DEVICE FOR DETECTING A REMODELING OR REVERSE REMODELING PHENOMENON OF THE PATIENT

(71) Applicant: SORIN CRM SAS, Clamart (FR)

(72) Inventors: Paola Milpied, Paris (FR); Marie-Anne Euzen, Bievres (FR)

(73) Assignee: Sorin CRM SAS, Clamart (FR)

( * ) Notice: Subject to any disclaimer, the term of this patent is extended or adjusted under 35 U.S.C. 154(b) by 160 days.

This patent is subject to a terminal disclaimer.

(21) Appl. No.: 16/576,521

(22) Filed: Sep. 19, 2019

(65) Prior Publication Data

US 2020/0009382 A1  Jan. 9, 2020

Related U.S. Application Data

(63) Continuation of application No. 15/701,249, filed on Sep. 11, 2017, now Pat. No. 10,420,945, which is a
(Continued)

(30) Foreign Application Priority Data

Apr. 17, 2015 (FR) ...................... 1553421

(51) Int. Cl.
*A61N 1/362* (2006.01)
*A61N 1/365* (2006.01)
(Continued)

(52) U.S. Cl.
CPC ............ *A61N 1/3627* (2013.01); *A61B 5/316* (2021.01); *A61B 5/318* (2021.01); *A61B 5/341* (2021.01);
(Continued)

(58) Field of Classification Search
CPC .......... A61B 5/283; A61B 5/316; A61B 5/318; A61B 5/341; A61B 5/361; A61B 5/686;
(Continued)

(56) References Cited

U.S. PATENT DOCUMENTS 5,193,535 A  3/1993  Bardy et al.
7,996,070 B2  8/2011  Van Dam et al.
(Continued)

FOREIGN PATENT DOCUMENTS

EP  2 105 843 A1  9/2009
EP  2 324 885 A1  5/2011
(Continued)

OTHER PUBLICATIONS

Milpied, et al., Implantable Cardioverter Arrhythmia Discrimination in Defibrillators using Support Vector Machines Applied to a new Representation of Electrograms, IEEE Tranactions on Biomedical Engineering, vol. 58, No. 6, Jun. 2011, 7 pages.
(Continued)

*Primary Examiner* — George Manuel
(74) *Attorney, Agent, or Firm* — Foley & Lardner LLP

(57) ABSTRACT

According to some embodiments, a device operates by comparative morphological analysis of depolarization signals collected in spontaneous rhythm on separate respective channels, with two temporal components combined into a single 2D parametric VGM vectogram characteristic. Similarity quantification methods evaluate a variation over time of a descriptor parameter of a current VGM compared to a stored previous reference VGM. This variation is compared with predetermined thresholds to diagnose an occurrence of remodeling or reverse remodeling in a patient, and/or to detect a lead failure or an occurrence of ischemia. The descriptor parameter is a function of a velocity vector of the VGM, a comparison relating to a correlation coefficient
(Continued)

between respective magnitudes of a current VGM velocity vector and of a reference VGM velocity vector, and an average angle between these respective velocity vectors.

20 Claims, 4 Drawing Sheets

Related U.S. Application Data continuation of application No. 15/130,540, filed on Apr. 15, 2016, now Pat. No. 9,757,566.

(51) Int. Cl.
*A61B 5/00* (2006.01)
*A61N 1/368* (2006.01)
*A61N 1/39* (2006.01)
*A61B 5/316* (2021.01)
*A61B 5/318* (2021.01)
*A61B 5/341* (2021.01)
*A61N 1/05* (2006.01)
*A61N 1/37* (2006.01)
*A61B 5/283* (2021.01)
*A61B 5/361* (2021.01)

(52) U.S. Cl.
CPC ............ *A61B 5/686* (2013.01); *A61N 1/0563* (2013.01); *A61N 1/365* (2013.01); *A61N 1/36842* (2017.08); *A61N 1/36843* (2017.08); *A61N 1/3702* (2013.01); *A61N 1/3925* (2013.01); *A61N 1/39622* (2017.08); *A61B 5/283* (2021.01); *A61B 5/361* (2021.01); *A61B 5/7246* (2013.01); *A61B 5/7275* (2013.01); *A61B 5/746* (2013.01); *A61N 1/3682* (2013.01); *A61N 1/3684* (2013.01)

(58) Field of Classification Search
CPC ..... A61B 5/7246; A61B 5/7275; A61B 5/746; A61N 1/0563; A61N 1/3627; A61N 1/365; A61N 1/3682; A61N 1/3684; A61N 1/36842; A61N 1/36843; A61N 1/3702; A61N 1/3925; A61N 1/39622
See application file for complete search history.

(56) References Cited

U.S. PATENT DOCUMENTS

| | | |
|---|---|---|
| 2007/0043394 A1 | 2/2007 | Zhang et al. |
| 2007/0123940 A1* | 5/2007 | Dorr ................. A61B 5/341 607/5 |
| 2007/0191901 A1 | 8/2007 | Schecter |
| 2007/0239037 A1 | 10/2007 | Ghio et al. |
| 2010/0042176 A1 | 2/2010 | Snell |
| 2010/0249626 A1 | 9/2010 | El Arab et al. |
| 2011/0118803 A1 | 5/2011 | Hou et al. |
| 2011/0118804 A1 | 5/2011 | Henry et al. |
| 2011/0152660 A1 | 6/2011 | Davenport et al. |
| 2011/0230776 A1 | 9/2011 | Milpied et al. |
| 2014/0172037 A1 | 6/2014 | Euzen et al. |

FOREIGN PATENT DOCUMENTS

| | | |
|---|---|---|
| EP | 2 368 493 A1 | 9/2011 |
| EP | 2 742 971 A1 | 6/2014 |
| EP | 2 742 973 A1 | 6/2014 |

OTHER PUBLICATIONS

Preliminary Search Report for French Patent Application No. 1553421, dated Oct. 21, 2015, 2 pages.

* cited by examiner

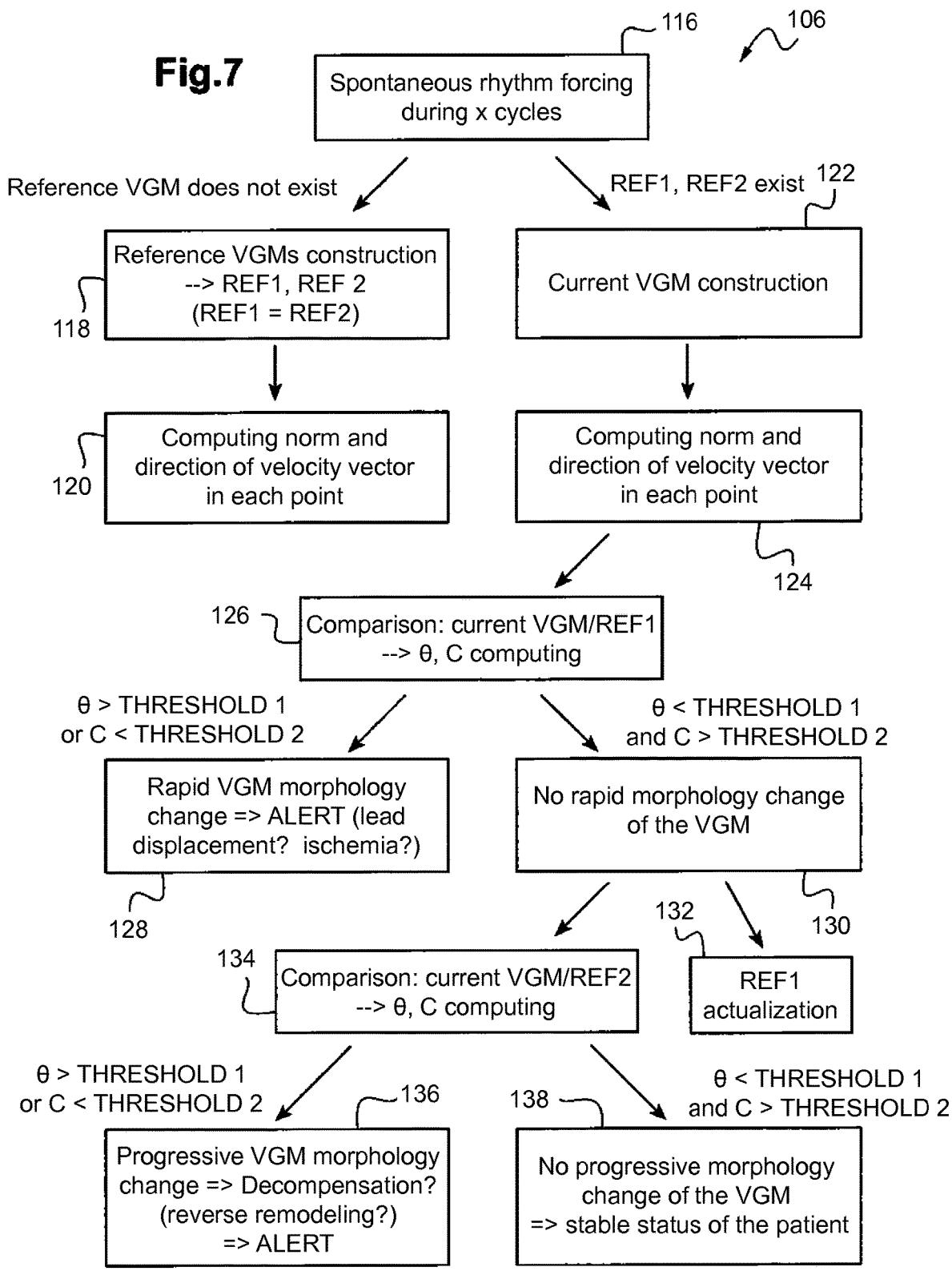

ACTIVE IMPLANTABLE MEDICAL DEVICE FOR DETECTING A REMODELING OR REVERSE REMODELING PHENOMENON OF THE PATIENT

CROSS-REFERENCE TO RELATED APPLICATIONS

This application is a continuation of U.S. patent application Ser. No. 15/701,249, filed Sep. 11, 2017, which is a continuation of U.S. patent application Ser. No. 15/130,540, filed Apr. 15, 2016, which claims the benefit of and priority to French Patent Application No. 1553421, filed Apr. 17, 2015, each of which are incorporated herein by reference in their entireties.

BACKGROUND

The invention relates to "active implantable medical devices" as defined by Directive 90/385/EEC of 20 Jun. 1990 of the Council of the European Communities, and more precisely implants that continuously monitor cardiac rhythm and deliver, if necessary, electrical stimulation, resynchronization and/or defibrillation pulses to the heart, in case of a rhythm disorder detected by the device.

Anti-bradycardia stimulation involves monitoring electrical potentials of depolarization of the myocardium, and controlled delivery of pulses to the atrium and/or to the ventricle. In the case of a cardiac resynchronization therapy (CRT), stimulation is applied jointly to both ventricles.

An embodiment is described more precisely in the context of an implant that continuously monitors the cardiac rhythm and delivers electrical pulses to the heart, if necessary, to stimulate the left and right ventricles jointly and permanently to resynchronize them. The technique is called CRT or bi-ventricular pacing (BVP).

This particular case does not, however, limit the disclosure, which by a number of its aspects, is also applicable to "single chamber" devices wherein detection/stimulation only occurs in the right ventricle, or "dual chamber" devices wherein detection/stimulation occurs only in the right ventricle and in the right atrium.

A CRT pacemaker is disclosed, for example, in EP 1108446 A1 (Sorin CRM), which describes a device for applying, between the respective moments of stimulation of the left and right ventricles, a variable interventricular delay (DVV or VVD), adjusted to resynchronize the contraction of the ventricles with fine optimization of the patient's hemodynamic status. The VVD can be zero, positive (the left ventricle is stimulated after the right ventricle) or negative (the right ventricle is stimulated after the left ventricle).

This CRT device further includes a classical dual chamber operating mode pacemaker, wherein the device monitors the ventricular activity after a spontaneous (P-wave) or stimulated (pulse A) atrial event and triggers a stimulation of the right ventricle (V pulse) if no ventricular spontaneous activity (R wave) has been detected at the end of a said atrioventricular delay (AVD).

The present disclosure relates more particularly to long term monitoring of the patient' cardiac status and how this status changes, in particular to diagnose the occurrence of the phenomenon referred to as "cardiac remodeling in the patient." Cardiac remodeling can be defined as all the changes of the heart generated in response to a disease, which is generally associated with a bad prognosis.

Indeed, clinical changes being possibly asymptomatic, it is common that the patient unconsciously adapts its activity to his/her clinical status. At the first sign of heart failure crises appearing due to stress, the patient may reduce his/her activity to avoid the occurrence of such crises. The symptoms no longer appear because the patient changed his/her behavior to avoid them, but the disease continues to progress.

Remodeling occurs in the long run by increasing the volume of the left ventricle, with deterioration in the ejection fraction and of the intraventricular pressure regime due to the decrease of contractility and/or the excessive pressure downstream and, ultimately, by a decrease in cardiac output resulting in serious consequences for the body when heart failure progresses. It is only when the heart failure hinders the patient even at rest when he/she will consult a physician or, in extreme cases, be admitted to emergency.

In summary, due to self-adjustment, the lack of symptoms experienced by the patient introduces a significant delay between the onset of clinical changes and diagnosis of these changes, which is often too late.

By stimulating both ventricles in a controlled method, the CRT therapy optimizes the contraction/relaxation cycle with a direct benefit of facilitating the heart activity, which can help stabilize the remodeling phenomenon and even counter it ("reverse remodeling"), with a better prognosis for the patient.

According to exemplary embodiments, the present disclosure provides diagnostic methods incorporated into a pacemaker (CRT or other) that would provide regular monitoring (e.g., daily) of the patient's condition, especially to monitor the evolution of a cardiac remodeling (deleterious) or of a reverse remodeling (beneficial). This monitoring should be early enough to allow rapidly taking appropriate actions (such as a change in a setting of therapy or switching of this therapy to another therapy if it is not effective), thus avoiding the unexpected occurrence of a crisis in the short and medium term. In the case of a detected sudden worsening, it may be possible to alert the doctor immediately, for example by remote transmission of a message to a remote monitoring site.

A reference technique for evaluating long-term changes in the patient's heart condition, and therefore for determining the effectiveness of therapy and possibly adjusting the stimulation parameters, is echocardiography with the measurement of the ventricular volume and estimate of the characteristic delays of the systole, in particular estimation of the opening time of the aortic valve. This procedure, however, must be implemented in hospitals and by qualified personnel. The procedure is long and expensive and cannot be applied as often as would be useful or necessary without interfering with the patient's daily life.

Automatic analysis techniques from the implantable device have also been proposed, for example, by US 2011/0152660 A1, wherein the worsening and improving of the patient are evaluated from the evolution of the interventricular conduction delay considered alone or in combination with the evaluation of the patient's activity and/or the presence of pulmonary edema.

This method is however very sensitive to the position of the leads, as well as how the heart remodels. Therefore, in some cases the analysis may not provide the desired information, in particular if no significant change in the conduction delay is observed along the measurement axis, while according to another axis a much larger variation could have been observed.

US 2007/0239037 A1 describes another technique, based on the measurement (by ultrasound) of the interventricular conduction delay prior to implantation of the device. It aims at predicting the response of a patient to a CRT therapy. The greater the initial interventricular conduction delay is, the more likely it is that a significant remodeling is present. This is, however, not a diagnostic tool to assess the long term evolution of a patient's condition, after implantation of the device.

US 2007/0043394 A1 describes a technique for diagnosis of heart failure by detecting a variation of the intracardiac impedance at a constant heart rate. The evolution of this parameter in the long term can be used to determine whether the heart remodels. The measurement of the intracardiac impedance is not however a stable parameter in the long term (several weeks or months), which renders the operation difficult for diagnostic purposes with a sufficient degree of certainty.

US 2009/0270747 A1 (U.S. Pat. No. 7,996,070 B2) operates by analyzing the electrocardiogram (ECG) collected by a subcutaneous implant. Changes in the morphology of the signals are detected and evaluated, distinguishing those related to the cardiac condition of the patient from those related to changes in position of the latter. But these teachings are not transferable to a cardiac implant collecting endocardial electrogram signals (EGM), which have a quite different morphology.

SUMMARY

An embodiment of the disclosure proposes a device, such as an implantable pacemaker provided with means of diagnosis of cardiac remodeling that can overcome the aforementioned drawbacks, allowing, in particular:

To avoid long and costly echocardiogram examinations, which provide only a late diagnosis, often several months after implantation;

To assess the patient remodeling to adjust the stimulation parameters early and robustly;

To set up early alerts of aggravated risk of decompensation or ischemia to prevent hospitalizations and modify in due time the therapies and treatments; and In general, to ensure proper delivery and effectiveness of the applied therapy.

Some embodiments, in addition to or alternatively of a diagnosis of remodeling or reverse remodeling manifesting as slow changes, detect sudden occurrence of phenomena such as ischemia or lead displacement likely to seriously endanger the patient, in order to generate an immediate corresponding alert.

More specifically, some embodiments provide a device including:

Means for controlled stimulation of the heart;

Means for detection of ventricular and/or atrial depolarization signals; and

Means of morphological analysis, adapted to compare depolarization signals collected on the same channel at separate moments.

In some embodiments, the morphological analysis includes:

Inhibiting the means for controlled stimulation;

Collecting at least two endocardial electrogram signals EGM concurrently on separate respective channels, during a spontaneous rhythm cardiac cycle, and deriving at least two respective distinct temporal components;

Combining the at least two temporal components in at least one 2D representative parametric characteristic of the cardiac cycle, based on variations of one of the temporal components as a function of the other;

Analyzing the 2D characteristic and deriving, from the 2D characteristic or from an average of the 2D characteristics collected over successive cardiac cycles, at least one representative intrinsic descriptor parameter of the 2D characteristic;

As a method of historical analysis, periodically evaluating the variation over time of the at least one intrinsic descriptor parameter of a current 2D characteristic with respect to a previous reference 2D characteristic stored by the device; and Comparing to at least a predetermined threshold variation measured by the historical analysis, and selectively triggering an alert depending on the result of the comparison.

According to various embodiments:

The historical analysis includes daily assessing of the variation over time of at least one intrinsic descriptor parameter;

The at least one intrinsic descriptor parameter is a function of the velocity vector of the 2D characteristic, considered at a plurality of respective points (Pi) of that characteristic;

The parameter may include the magnitude of the velocity vector with the historical analysis including calculating a correlation coefficient between the magnitudes of the respective velocity vectors of the current 2D characteristic and of the 2D reference characteristic;

The parameter can also include the direction of the velocity vector, with the historical analysis including calculating the average angle between the respective velocity vectors of the current 2D characteristic and of the 2D reference characteristic;

The comparison may include i) the average angle between velocity vectors to a first threshold and ii) the correlation coefficient between the magnitudes of the velocity vectors to a second threshold; the method further includes triggering the alert when both i) the average angle between the velocity vectors is greater than the first threshold or ii) the correlation coefficient between the magnitudes of the velocity vectors is less than the second threshold;

The morphological analysis further includes, in the absence of triggering of the alert based on the comparison, updating the at least one intrinsic parameter descriptor of the reference 2D characteristic The device further includes diagnostic means of remodeling or of reverse remodeling, implementing the morphological analysis, the alert triggered by the comparison being an alert of occurrence of remodeling or reverse remodeling in the patient; and The device further includes means of detecting the lead break or of ischemia diagnosis implementing the morphological analysis, the alert triggered by the comparison being a lead break alert or an alert of occurrence of ischemia in the patient.

In another embodiment, the EGM signals collected concurrently on separate respective channels include:

An unipolar EGM far-field signal collected between i) a proximal or distal electrode or, where appropriate, an intermediate electrode or a defibrillation coil of a ventricular lead and ii) the metal housing of the generator device, or between i) a first proximal electrode or distal electrode or defibrillation coil and ii) a second proximal electrode, or distal electrode or, where appropriate an intermediate electrode or a defibrillation coil, respectively of two separate ventricular leads located both in the same ventricle, or between i) a first proximal electrode or distal electrode or defibrillation coil and ii) a second proximal electrode, or distal electrode or intermediate electrode, respectively from a right ventricular lead and from a left ventricular lead; and A bipolar near-field EGM signal collected between i) a distal electrode and ii) a proximal electrode of a ventricular lead, or between i) a defibrillation coil and ii) a distal or proximal electrode of said ventricular lead, or between i) a distal electrode and ii) an intermediate electrode of a left ventricular lead or between i) a proximal electrode and ii) an intermediate electrode of said left ventricular lead, or between two intermediate electrodes of said left ventricular lead.

BRIEF DESCRIPTION OF THE DRAWINGS

Further features, characteristics and advantages of the present disclosure will become apparent to a person of ordinary skill in the art from the following detailed description of preferred embodiments of the present disclosure, made with reference to the drawings annexed, in which like reference characters refer to like elements and in which:

FIG. 7 is a diagram showing a sequence of steps performed during patient follow-up, to determine the evolution of his/her condition, including the occurrence of remodeling or of reverse remodeling.

DETAILED DESCRIPTION

An embodiment of the device will now be described.

Regarding its software aspects, the invention may be implemented by appropriate programming of the controlling software of a known stimulator, for example a cardiac pacemaker, including methods for acquisition of a signal provided by endocardial leads and/or one or several implantable sensors.

The disclosure may notably be applied to implantable devices, such as that of the Reply, Paradym, Intensia, Paradym RF and Platinium families, manufactured and commercialized by Sorin CRM, Clamart, France.

These devices include programmable microprocessor circuitry to receive, format and process electrical signals collected by implantable electrodes, and deliver stimulation pulses to these electrodes. It is possible to download in it by telemetry software that is stored in memory and executed to implement the functions of the embodiment of the disclosure that are described below. The adaptation of these devices to the implementation of the functions of the disclosure is within the skill in the art and will not be described in detail.

In some embodiments, a method of the disclosure is implemented primarily by software, by appropriate algorithms automatically and repeatedly executed by a microcontroller or a digital signal processor. For the sake of clarity, the various processing applied are broken down schematically by a number of distinct functional blocks, but this representation, however, has only illustrative purpose, these circuits including common elements and corresponding in practice to a plurality of functions generally performed by the same software.

Figure 1:
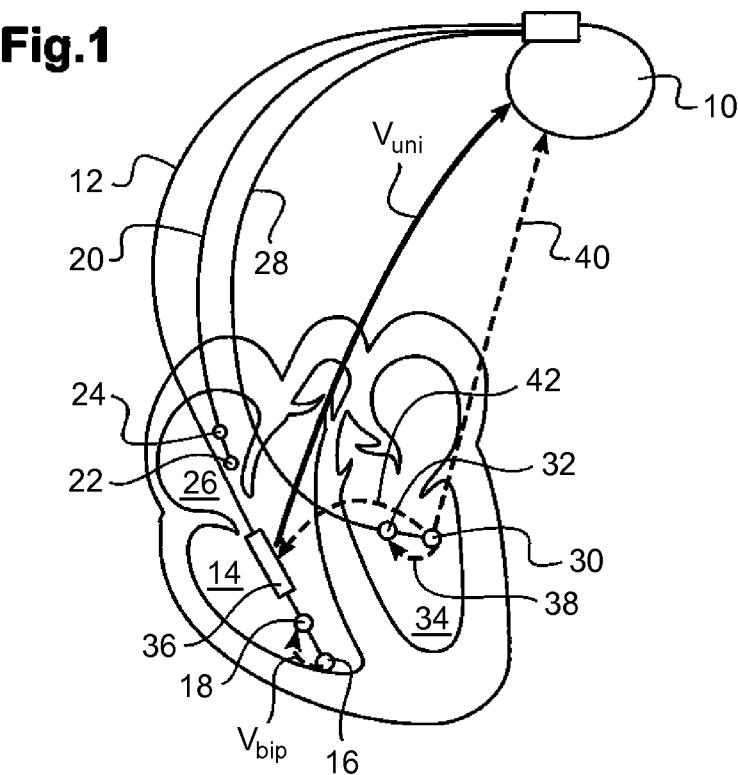
FIG. 1 is a general view showing a CRT device with its generator and right and left cardiac leads implanted in the heart.

FIG. 1 illustrates a typical configuration of CRT stimulation where a pulse generator 10 is associated with a first lead 12 located in the right ventricle 14. The head of the lead includes two electrodes, namely a distal electrode (tip) 16 and a proximal electrode (ring) 18. A second lead 20 is provided with atrial electrodes for distal detection 22 and proximal detection 24 located at the right atrium 26 for the detection of signals in this cavity and the possible application of atrial stimulation.

To allow bi-ventricular pacing to restore the synchronization between the two ventricles, the device is provided with a third lead 28, for example a lead disposed in the coronary network, including one or more electrodes 30, 32 disposed in the vicinity of the left ventricle 34. In addition to the illustrated distal and proximal electrodes 30, 32, the left lead may also include one or more intermediate electrodes located in a middle position between the electrodes 30 and 32. It is thus possible to ensure the stimulation, concomitantly or controlled with a slight delay (interventricular delay DVV), on both the right and left ventricles to restore the synchronization between the two cavities and improve overall patient hemodynamics (in the case of a left multi-electrode lead, a left multisite pacing can also be applied to treat a disorder of intraventricular synchrony).

The right ventricular lead 12 may also be provided with a winding (coil) 36 forming a ventricular defibrillation electrode and for also collecting an endocardial signal (this coil could possibly replace the proximal ring electrode 18).

With specific regard to the stimulation of the left ventricle, it is possible to use a bipolar (between the two electrodes 30 and 32 of the lead 28) or an unipolar (between one of the electrodes 30 or 32 and the housing of the generator 10 can) configuration of the generator 10. The two corresponding "stimulation vectors" are referenced 38 and 40 in FIG. 1. These same vectors can also be used for collecting a left ventricular depolarization signal. Note that in the case of a multipolar lead there are a large number of bipolar and unipolar vectors, possible defined from each of the electrodes (one can also simultaneously use multiple left vectors, in the case mentioned above of a left multisite pacing).

Embodiments of the disclosure will now be explained in this context.

According to some embodiments, the long term evolution of the morphology of cardiac signals collected in the patient's spontaneous rhythm may be monitored (in the absence of any stimulation applied by the device), for example by a daily assessment, for detecting:

Slow variations of the morphology, which would reveal an appearance of such a remodeling (with dilatation of the ventricles, deleterious to the patient) or a reverse remodeling (with decrease in ventricular volume, beneficial to the patient), and/or Sudden variations, caused by sudden onset phenomena such as ischemia or lead displacement, that might seriously endanger the patient, to generate an alert without delay.

More specifically, to overcome the disadvantages of known techniques that have been referenced in the background, according to some embodiments, the present disclosure proposes to combine two endocardial electrogram signals (EGM) collected in the patient's intrinsic rhythm, especially the signals from the same ventricular cavity, e.g., the right ventricle.

In order to determine if the spontaneous rhythm condition is met, signal analysis is performed during a time interval wherein no stimulation is issued (in the case of stimulation on demand) or for a forced inhibition short period of the stimulation by the device.

The EGMs collected for this purpose in the right ventricle may include for example (see FIG. 1):

A right ventricular component Vbip, derived from a bipolar near-field EGM signal collected between the distal electrode 16 and the proximal electrode 18 of the right ventricular lead 12, and Another right ventricular component Vuni, derived from a unipolar EGM far-field signal collected between the defibrillation coil 36 of the right ventricular lead 12 and the metal housing of the generator 10.

Figure 2:
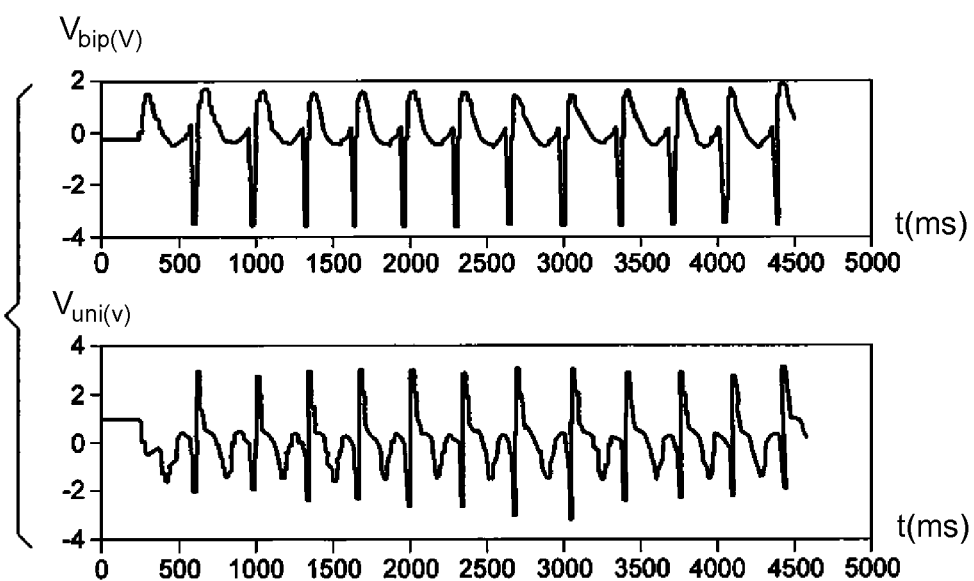
FIG. 2 is an example of EGM signals obtained respectively on bipolar ventricular and unipolar ventricular channels of one of the leads of FIG. 1.

FIG. 2 illustrates an example of EGM plots, Vbip and Vuni, respectively observed on the ventricular bipolar channel and on the ventricular unipolar channel of the configuration of FIG. 1.

Other configurations can be used, from far-field signals (e.g. between one of the electrodes 16 or 18 and the housing 10) and from near-field signals (between two electrodes of the same ventricular lead).

This configuration (signals from the right cavity) is, however, not limiting. In some cases, for example for a patient with a left bundle branch block (LBBB) without right conduction problem, the effect of remodeling will not be apparent on the collected signals in the right cavities. In such a case, one should analyze components derived, for example, from a left ventricular bipolar signal and an inter-ventricular signal, or from a left bipolar signal and a left unipolar signal. The bipolar component would be collected for example between the electrodes 30 and 32 of the left ventricular lead 28 (referenced as 38), and the unipolar component between the tip electrode 30 (or the ring electrode 32) and the can housing of the generator 10 (referenced as 40). Alternatively, the unipolar component may also be collected between the tip electrode 30 (or the ring electrode 32) of the left ventricular lead 28 and the coil winding 36 of the right ventricular lead 12 (referenced as 42).

In the long term, if comparisons are made at the time of implantation, three months after implantation and one year after implantation, the signal shape changes over time, but in some cases, or in some patients, the unipolar signal Vuni does not really provide any information that changes over time, while the bipolar signal Vbip contains much more meaningful information. Conversely, in other cases, the change is very late in the bipolar signal Vbip and the unipolar channel Vuni (between the coil winding 36 and the housing 10 can of the generator) gives the desired information, in a much earlier and discriminant method.

To overcome this drawback, the disclosure proposes to combine both bipolar and unipolar components, in a unique feature containing, more broadly, all available information in order to conduct a complete and robust assessment of the patient's condition through time.

This combination of both bipolar and unipolar signals is designed as a "heart loop" or "vectogram" (VGM), which is the representation in a two-dimensional space of one of two EGM signals (on the ordinate) versus the other (on the abscissa). Each cardiac cycle is then represented by a vectogram {Vbip, Vuni} in the plan thus defined, a vectogram whose geometry (shape of the curve) is independent of the temporal dimension (which only intervenes as a parameter describing how the curve is traversed).

It is emphasized that VGM, which is obtained from electrogram (EGM) signals from intracardiac leads should not be confused with the "vectocardiogram" (VCG), which is obtained from electrocardiogram (ECG) signals from external electrodes placed on the patient's chest.

The construction of a VGM and its analysis to quantify cardiac data are described for example in Milpied et al., "Implantable Cardioverter Arrhythmia Discrimination in Defibrillators using Support Vector Machines Applied to a new Representation of Electrograms," IEEE Transactions on Biomedical Engineering, June 2011, 58 (6): 1797-1803.

Analysis of a VGM for different purposes other than those of the present disclosure has already been proposed in particular from EP 2105843 (ELA Medical) for discriminating between ventricular tachycardia and supraventricular; from EP 2324885 A1 (Sorin CRM) for invalidating a capture test in case of fusion, that is to say of simultaneous stimulation triggered to spontaneous depolarization; from EP 2368493 A1 (Sorin CRM) for discrimination of noise artifacts for the validation or invalidation of cardiac cycles to be analyzed; from EP 2742971 A1 (Sorin CRM) to determine the presence or absence of an evoked wave induced by the stimulation of a cavity; or from EP 2742973 A1 (Sorin CRM) for the detection of the possible presence of an anodal stimulation phenomenon.

But in all these cases, the purpose is to analyze a single cardiac cycle, to reveal a characteristic of this cycle (type of arrhythmia, presence or absence of a capture, artifact, etc.). It is not, as in the present disclosure, to make a historical analysis to determine the appearance of more or less rapid variations in the long term, of a particular characteristic of the VGM, including for the purpose of diagnosis of a patient's evolutionary status.

Figure 3:
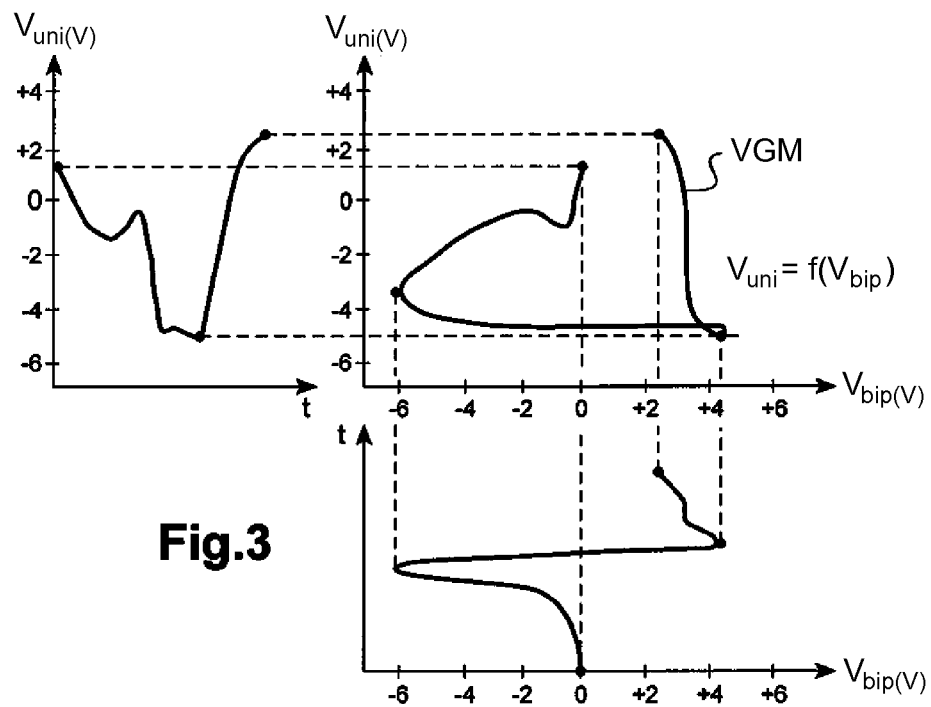
FIG. 3 shows the method to combine the bipolar and unipolar signals collected in a single ventricular cavity to construct a two-dimensional vectogram characteristic, independent of time.

Specifically, as shown in FIG. 3, the collected EGM signals Vuni(t) and Vbip(t) are sampled, and the successive samples of the two components are stored and then combined to produce a parametric curve (the VGM characteristic) of the type VGM=(Vbip(t), Vuni(t)) or {x=Vbip(t), y=Vuni(t)}.

This curve is parameterized by time, plotted on the basis of changes in one of the temporal components (Vuni) as a function of the other (Vbip). It constitutes a vectogram (VGM) representative of the cardiac cycle to be analyzed, and is also referred to as the "parametric 2D characteristic." It graphically shows the shape of a loop, the time only appearing in the manner in which the loop is traversed over the cycle duration.

Note that the two-dimensional (2D) analysis discussed here should not be understood in a limiting manner. The disclosure can indeed be applied equally to an analysis in higher order multi-dimensional space (3D or more), by extrapolating the teachings of the present description to a situation where EGM signals from the same cavity are simultaneously collected on three or more channels.

Figure 4:
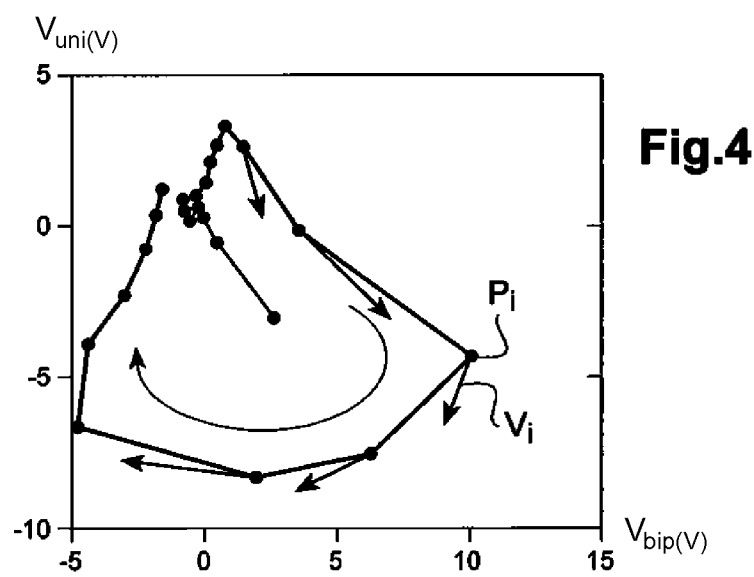
FIG. 4 is an example of sampled vectogram obtained for a cardiac cycle sampled at 128 Hz, with representation of the velocity vectors in successive various points.

In practice, as shown in FIG. 4, the sampling produces an open polygon VGM where each vertex corresponds to a sampling point of the measurement of the signals Vuni and Vbip of the EGM. In the example of FIG. 4, the sampling is carried out at a frequency of 128 Hz, which gives about 11 measurement points for a time interval of 80 ms, which are values that can be stored for analysis.

The shape of the velocity vector Vi in various successive points Pi of the VGM for a sampling frequency of 128 Hz is also shown in FIG. 4. At a given point, the velocity is a vector data (the velocity being defined by its orientation and its magnitude), and the velocity vector can be computed at each point of the VGM from a discrete filter that approximates the first derivatives Vbip(t)/dt and Vuni(t)/dt which, for a sampled characteristic, can be calculated from the previous point and the next point on the curve.

The collected VGM characteristic is stored as a series of descriptor parameters based on the velocity vector at each point of the curve and including i) the magnitude of the velocity vector and ii) the orientation of the velocity vector, i.e. the angle it makes with respect to the axis of the abscissa of the VGM.

An embodiment of the disclosure proposes to operate a morphological comparison between the current VGM (stored as the values of the angle and of the magnitude of the velocity vectors at different sampling points) with a reference VGM (stored as counterpart descriptors).

The comparison between these two VGMs is to quantify the similarities from:

The correlation coefficient C between the magnitude of the respective velocity vectors of the current VGM and the reference VGM and The average value $\theta$ of the angle formed between them the respective velocity vectors of the current VGM and of the reference VGM.

The curves may be considered similar if C (which reflects the correlation between the norms of the velocity vectors) is large enough and $\theta$ (which reflects the deviation of the orientation angles) is small enough.

A simple threshold can then be set for each descriptor (THRESHOLD1 for the angle and THRESHOLD2 for the correlation coefficient) to conclude on the similarity of the curves:

If $\theta$ is below THRESHOLD1 and C above THRESHOLD2, it will be considered that the curves are similar, If $\theta$ exceeds THRESHOLD1 or C is less than THRESHOLD2, it will be assumed that the curves are different.

Remodeling or reverse remodeling should not abruptly change the morphology of the collected spontaneous rhythm of the EGMs. If there are different curves, an anomaly may have occurred.

Another embodiment of the disclosure proposes to detect possible changes in the morphology of the EGMs, whether these changes are sudden, or whether they are progressive.

In the case of a sudden and significant change of morphology, it may be considered that the patient is in danger, such change revealing a serious problem such as lead displacement, ischemia, etc. It may then be desirable to trigger an alert.

Incremental, but minor, changes of morphology may occur after the first months following implantation, and may be due, for example, to the maturation of the leads. No special action may need to be taken in this case.

However, changes due to a remodeling or to a reverse remodeling will also be gradual, but more important. If these particular phenomena are to be highlighted, appropriate thresholds are simply to be chosen, e.g. determined beforehand from a learning base.

Figure 5:
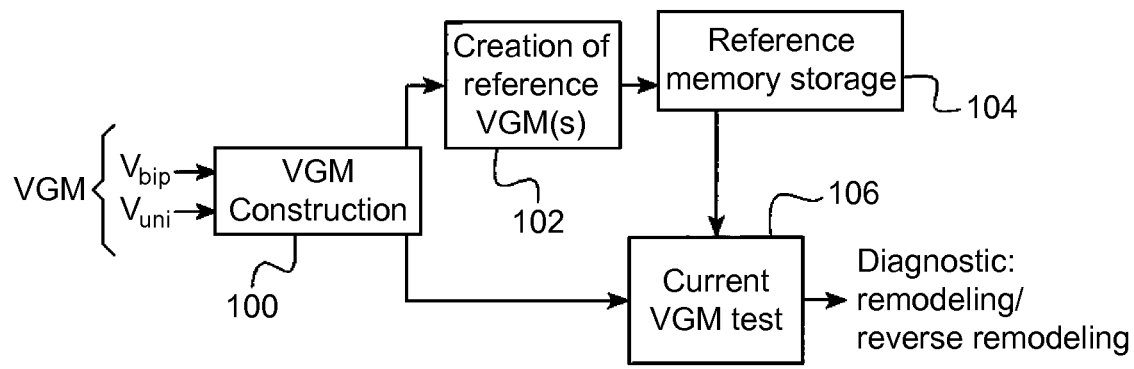
FIG. 5 is a block diagram illustrating an implementation of the disclosure.

FIG. 5 illustrates, in very general terms a method in which the device of the disclosure is implemented.

The current VGM is built periodically, for example once a day or once a week, under stable conditions (slow sinus rhythm, preferably overnight), and then stored and compared to a reference VGM created at initialization of the therapy, and possibly updated in case of alert or of decompensation, or manually by the practitioner during a follow-up visit for example.

From the collected bipolar and unipolar EGMs, a VGM is built (block 100). Initially, one (or more) reference VGM(s) is (are) constructed (block 102, detailed in FIG. 8) and stored in memory (block 104). Similarly, periodically (e.g., daily), a current VGM is constructed and compared to the stored reference (block 106) to derive an indicator of the long term evolution of the patient's condition (remodeling, reverse remodeling or non scalable state) and/or the sudden onset of severe phenomena such as lead break or ischemia.

Figure 6:
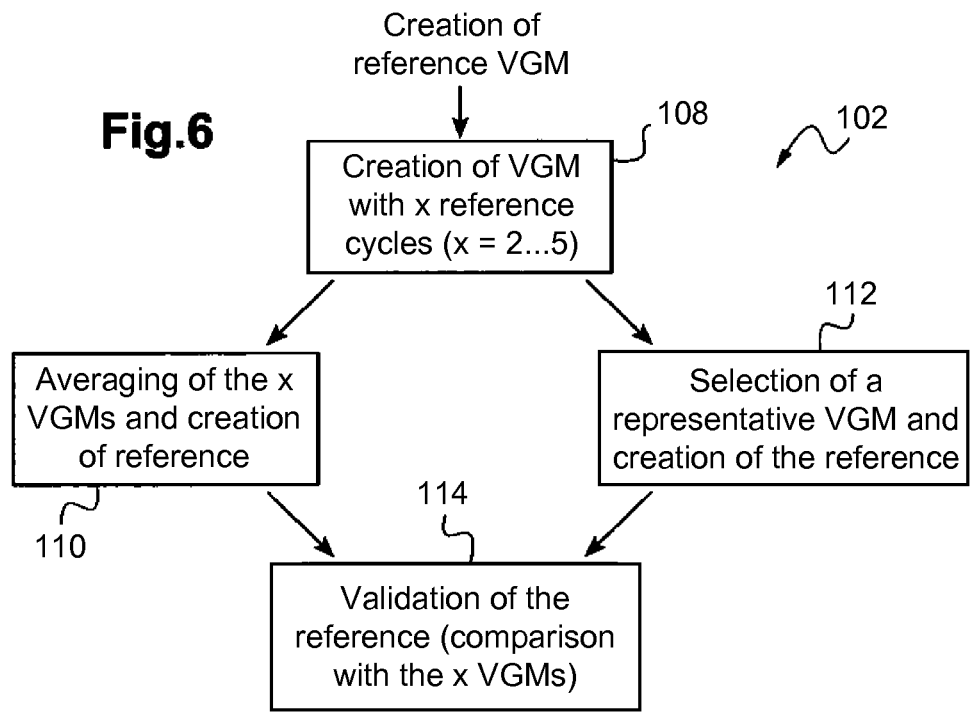
FIG. 6 is a diagram showing a sequence of steps executed during a preliminary preparation of the references.

FIG. 6 illustrates the creation of a reference VGM (block 102 of FIG. 5).

This reference is created from a plurality of representative cardiac cycles (no artifact of extrasystole, no fusion, etc.), for example x=2 to 5 cardiac cycles, for which each of the VGMs are constructed and the descriptor parameter vector is calculated (block 108). These data are then averaged (block 110) or, alternatively, one of the most representative cardiac cycles is selected to be the reference (block 112). From the averaged or selected VGM, the reference is validated (block 114), by comparing it to each cycle collected in step 108, so as to verify that the difference between this reference and each of the other cycles remains within acceptable limits, or ensuring that it remains within those limits for a sufficient, predetermined, number of the cycles.

FIG. 7 illustrates the sequence of the various operations of the test of the current VGM (block 106 of FIG. 5) performed at regular intervals, for example daily.

The first step (block 116) is the inhibition of any stimulation by the device in order to allow a spontaneous rhythm for a predetermined number x of cycles.

If no reference VGM is available at this stage, one or more reference VGMs corresponding to the patient's condition should be created. In the illustrated example, two reference VGMs REF1, REF2 are created:

Reference VGM REF1 is intended to highlight abrupt changes in morphology resulting from a lead displacement or from the onset of ischemia, while Reference VGM REF2 will be aimed at highlighting progressive morphological changes related to the possible emergence of remodeling or of reverse remodeling; this VGM may be determined once and for all and may not be changed automatically.

The reference VGMs REF1 and REF2 are constructed as explained above with reference to FIG. 6, initially with REF1=REF2 (block 118). In the case of sampling at 128 Hz, the VGM is for example built over an interval of about 80 ms centered on the depolarization peak of the right ventricle, from 11 successive samples. The magnitudes and directions of the VGM velocity vectors are determined and stored (block 120).

If at the end of step 116 references REF1 and REF2 are available in memory, then the device builds the current VGM (block 122) and determines the magnitude and direction of the velocity vector at each point of this VGM (block 124), in the same method as in blocks 118 and 120 corresponding to the reference VGMs.

The next step (block 126) is to calculate the descriptors C (correlation coefficients between the magnitudes of the velocity vectors) and $\theta$ (mean angle between the velocity vectors) representative of the comparison between the current VGM and the reference VGM REF1.

If the condition $\theta$>THRESHOLD1 or C<THRESHOLD2 is fulfilled (block 128), an abrupt change in morphology has occurred and triggering an alert is justified, such as remote transmission of a message to a remote site to alert a physician of on a phenomenon such as lead displacement or ischemia onset.

If the above condition is not satisfied, that is to say if θ<THRESHOLD1 and C>THRESHOLD2 (block 130), it is considered that there was no rapid change in morphology. The reference VGM REF1 is then updated by replacing it by the current VGM value (block 132), and the device then seeks to highlight progressive morphological changes that could reveal remodeling or reverse remodeling.

To this end, the descriptors C and θ are calculated (block 134) in the same method as in block 126, but this time by comparing the current VGM to the reference VGM REF2.

If the condition θ>THRESHOLD1 or C<THRESHOLD2 is met (block 136), it is considered that there has been a significant change in the morphology, which may suggest a remodeling. An alert may eventually be issued, corresponding to the result.

For deciding whether an alert is necessary, other parameters may be taken into account, such as the width of the QRS complex of the current EGM (this width being calculated as the time elapsed between the beginning and end of the detected depolarization), or one or more derived parameters of an endocardial acceleration signal (EA), or also the interventricular conduction delay. Indeed, a significant shortening of the width of the QRS complex is probably due to a reverse remodeling (which does not justify an alert) as well as an increase in the amplitude of the peak of endocardial acceleration or a decrease in the interventricular conduction delay.

In any contrary case, that is to say if θ<THRESHOLD1 and C>THRESHOLD2 (block 138), it is considered that there were no changes, neither sudden nor gradual, of the VGM morphology. Therefore, the patient's condition is stable, without worsening or improvement.

What is claimed is:

1. An implantable medical device comprising:
   one or more circuits configured to:
      collect two endocardial electrogram (EGM) signals during a spontaneous rhythm cardiac cycle, wherein the EGM signals include a unipolar far-field EGM signal and a near-field EGM signal;
      derive a temporal component from each of the EGM signals;
      combine the two temporal components into a parametric 2D characteristic representative of the cardiac cycle based on the variations of one of the temporal components as a function of the other temporal component;
      analyze the 2D characteristic by deriving an intrinsic descriptor parameter representative of the 2D characteristic; and
      evaluate a variation over time of the intrinsic descriptor parameter of the 2D characteristic with respect to a previous reference 2D characteristic stored by the device to determine a condition of a patient.

2. The device of claim 1, wherein the EGM signals are collected concurrently.

3. The device of claim 1, wherein the variation over time is evaluated periodically.

4. The device of claim 1, wherein the intrinsic descriptor parameter is a function of a velocity vector of the 2D characteristic, considered in a plurality of respective points of the 2D characteristic.

5. The device of claim 4, wherein the function of the velocity vector comprises a magnitude of the velocity vector.

6. The device of claim 5, wherein the processor is configured to evaluate the variation over time by calculating a correlation coefficient between the magnitudes of respective velocity vectors of the current 2D characteristic and the reference 2D characteristic.

7. The device of claim 6, wherein the function of the velocity vector comprises an orientation of a speed vector.

8. The device of claim 7, wherein the processor is configured to evaluate the variation over time by calculating an average angle between the velocity vectors of the current 2D characteristic and of the reference 2D characteristic.

9. The device of claim 8, wherein the evaluation comprises:
   comparing the average angle between velocity vectors to a first threshold;
   comparing the correlation coefficient between the magnitudes of velocity vectors to a second threshold; and
   selectively triggering an alert when the average angle between velocity vectors exceeds the first threshold or the correlation coefficient between the magnitudes of velocity vectors is lower than the second threshold.

10. The device of claim 1, wherein the processor is configured to selectively update the intrinsic descriptor parameter of the reference 2D characteristic based on the determined condition of the patient.

11. The device of claim 1, wherein the processor is further configured to perform diagnostics of remodeling or of reverse remodeling, and to trigger an alert based on an occurrence of remodeling or of an occurrence of reverse remodeling in the patient.

12. The device of claim 1, wherein the processor is further configured to detect at least one of a breakage of a lead or to diagnose ischemia, and to trigger an alert indicating a lead break condition or an ischemia condition of the patient.

13. The device of claim 1, wherein the unipolar EGM far-field signal is collected between a first location comprising one or more of a proximal electrode, a distal electrode, an intermediate electrode, or a defibrillation coil electrode of a ventricular lead and a second location comprising a metal housing generator of the device.

14. The device of claim 1, wherein the unipolar EGM far-field signal is collected between a first location comprising one or more of a first proximal electrode, a first distal electrode, or a first defibrillation coil electrode of a first ventricular lead and a second location comprising a second proximal electrode, a second distal electrode, an intermediate electrode, or a second defibrillation coil electrode of a second ventricular lead, wherein both the first and the second ventricular leads are located in a single ventricle.

15. The device of claim 1, wherein the unipolar EGM far-field signal is collected between a first location comprising one or more of a first proximal electrode, a first distal electrode, or a first defibrillation coil electrode of a first ventricular lead and a second location comprising at least one of a second proximal electrode, a second distal electrode, or an intermediate electrode of a second ventricular lead, wherein the first ventricular lead is located in the right ventricle and the second ventricular lead is located in the left ventricle.

16. The device of claim 1, wherein the near-field EGM bipolar signal is collected between at least one of:
   a distal electrode and a proximal electrode of a ventricular lead;
   a defibrillation coil and at least one of the proximal electrode or the distal electrode of the ventricular lead;
   a distal electrode and an intermediate electrode of a left ventricular lead;
   a proximal electrode and the intermediate electrode of the left ventricular lead; or a first intermediate electrode and a second intermediate electrode of the left ventricular lead.

17. A method comprising:
collecting two EGM signals during a spontaneous rhythm cardiac cycle, wherein the EGM signals include a unipolar far-field EGM signal and a near-field EGM signal;
deriving a temporal component from each of the GMS signals;
combining the two temporal components into a parametric 2D characteristic representative of the cardiac cycle based on the variations of one of the temporal components as a function of the other temporal component;
analyzing the 2D characteristic by deriving an intrinsic descriptor parameter representative of the 2D characteristic; and
evaluating a variation over time of the intrinsic descriptor parameter of the 2D characteristic with respect to a previous reference 2D characteristic stored by the device to determine a condition of a patient.

18. The method of claim 17, wherein the EGM signals are collected concurrently.

19. The method of claim 17, wherein the variation over time is evaluated periodically.

20. The method of claim 17, wherein the intrinsic descriptor parameter is a function of a velocity vector of the 2D characteristic, considered in a plurality of respective points of the 2D characteristic.

* * * * *